United States Patent [19]

Eddington

[11] Patent Number: 4,617,913

[45] Date of Patent: Oct. 21, 1986

[54] ARTIFICIAL HEARING DEVICE AND METHOD

[75] Inventor: Donald K. Eddington, Belmont, Mass.

[73] Assignee: The University of Utah, Salt Lake City, Utah

[21] Appl. No.: 664,163

[22] Filed: Oct. 24, 1984

[51] Int. Cl.⁴ ........................................... H04R 23/00
[52] U.S. Cl. .............................. 128/1 R; 128/419 R; 179/107 R
[58] Field of Search .................. 128/1 R, 419 R, 782; 179/107 R, 107 FD

[56] References Cited

U.S. PATENT DOCUMENTS

| Re. 31,031 | 9/1982 | Kissiah, Jr. | |
|---|---|---|---|
| 3,715,605 | 8/1973 | Michelson | 128/1 R |
| 4,207,441 | 6/1980 | Ricard et al. | |
| 4,267,410 | 5/1981 | Forster et al. | |
| 4,284,856 | 8/1981 | Hochmair et al. | |
| 4,357,497 | 11/1982 | Hochmair et al. | |
| 4,366,349 | 12/1982 | Adelman | 179/107 FD |
| 4,400,590 | 8/1983 | Michelson | 179/107 FD |
| 4,403,118 | 9/1983 | Zollner et al. | 179/107 FD |
| 4,419,995 | 12/1983 | Hochmair et al. | |
| 4,495,384 | 1/1985 | Scoll et al. | 128/784 X |
| 4,515,158 | 5/1985 | Patrick et al. | 179/107 R |

FOREIGN PATENT DOCUMENTS 2811120 9/1978 Fed. Rep. of Germany ... 128/419 R

OTHER PUBLICATIONS

Dillier et al., "Computer Controlled . . . Implanter Multielectrodes," Scand. Audiol. Suppl. 11 (1980) pp. 163-170.
Hochmair, "Implanted Auditory . . . for the Deaf," Med. & Biol. Eng. & Comput., 3/1981, pp. 141-148.
Eddington, "Multiple Channel Intracochlear Stimulation", Neurological Surgery of the Ear and Skull Base, pp. 199-205, 1982.
Eddington, "Speech Recognition in Deaf Subjects with Multichannel Intracochlear Electrodes", Annals of NY Academy of Sciences, 1983, pp. 241-257.
Hochmair et al., "Cochlear Prostheses an International Symposium", Annals of NY Academy of Sciences, vol. 405, pp. 268-279, 1983.
Hochmair, "Aspects of Sound Signal Processing Using the Vienna Intra- and Extracochlear Implants", Cochlear Implants, 1985, pp. 101-110.
Eddington, "Auditory Prostheses Research with Multiple Channel Intracochlear Stimulation in Man", The Annals of Otology, etc., Supplement 53-vol. 87, Nov.--Dec., 1978, No. 6, Part 2, pp. 1-39.
Eddington, "Speech Discrimination in Deaf Subjects with Cochlear Implants", J. Acoust. Soc. Am., vol. 68, No. 3, 9/80, pp. 885-891, 1980.
Merzenich et al., "The UCSF Cochlear Implant Project", Adv. Audiol., vol. 2, pp. 119-144 (Karger, Basel, 1984).
Hochmair-Desoyer et al., "An Eight Channel Scala Tympani Electrode for Auditory Prostheses", IEE Trans. Biomed. Eng., vol. BME-27, No. 1, 1980, pp. 44-50.
Eddington et al., "Speech Recognition in a Deaf Subject with a Portable Multichannel Cochlear Implant System", Adv. Audiol., vol. 2, pp. 61-67, (1984).
Kiang et al., "Fundamental Considerations in Designing Auditory Implants", Acta Otolaryngol, 87:204-218, 1979.

Primary Examiner—Edward M. Coven
Attorney, Agent, or Firm—Spensley Horn Jubas & Lubitz

[57] ABSTRACT

An electronic hearing device for stimulating the auditory nerve by way of implanted electrodes wherein sound signals are converted to electrical signals which are divided into separate channels according to their frequencies. The signals of each channel are amplified and applied to the electrodes. The relative amplifications of each channel, after taking into account a threshold amplification, have a ratio of 6 to 7 dB/octave from the channel having the lowest center frequency to the channel having the highest center frequency.

19 Claims, 6 Drawing Figures

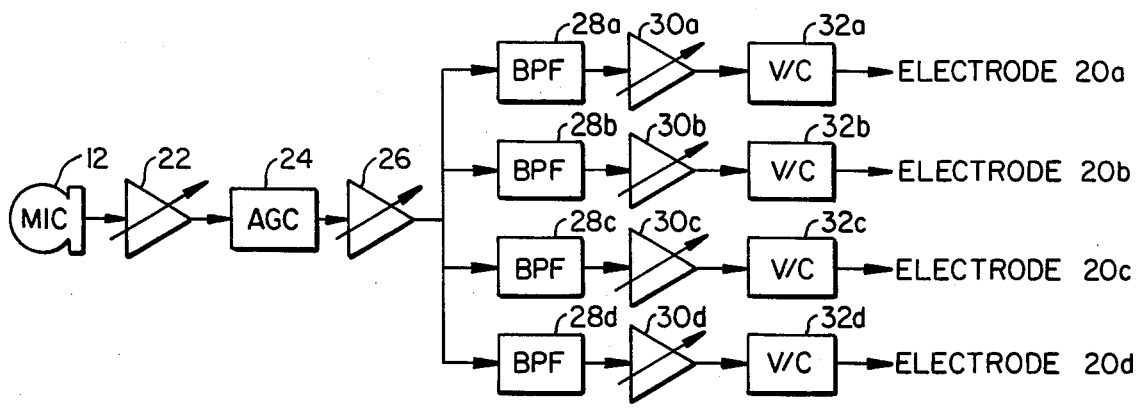
FIG._1.
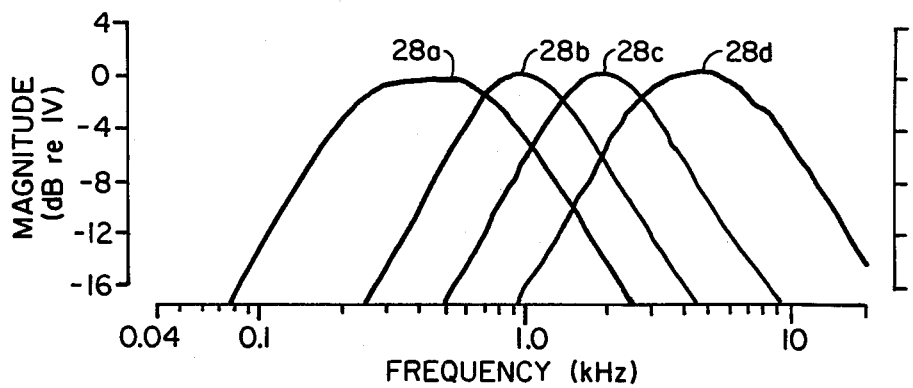
FIG._2.
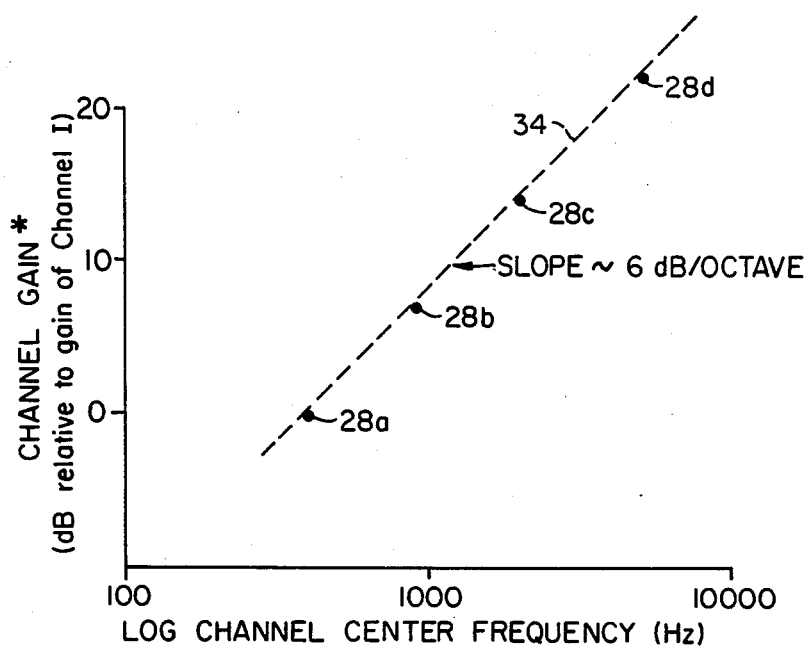
FIG._3. *(The channel gains are normalized for electrode threshold measured with a 200 Hz, stimulus.)

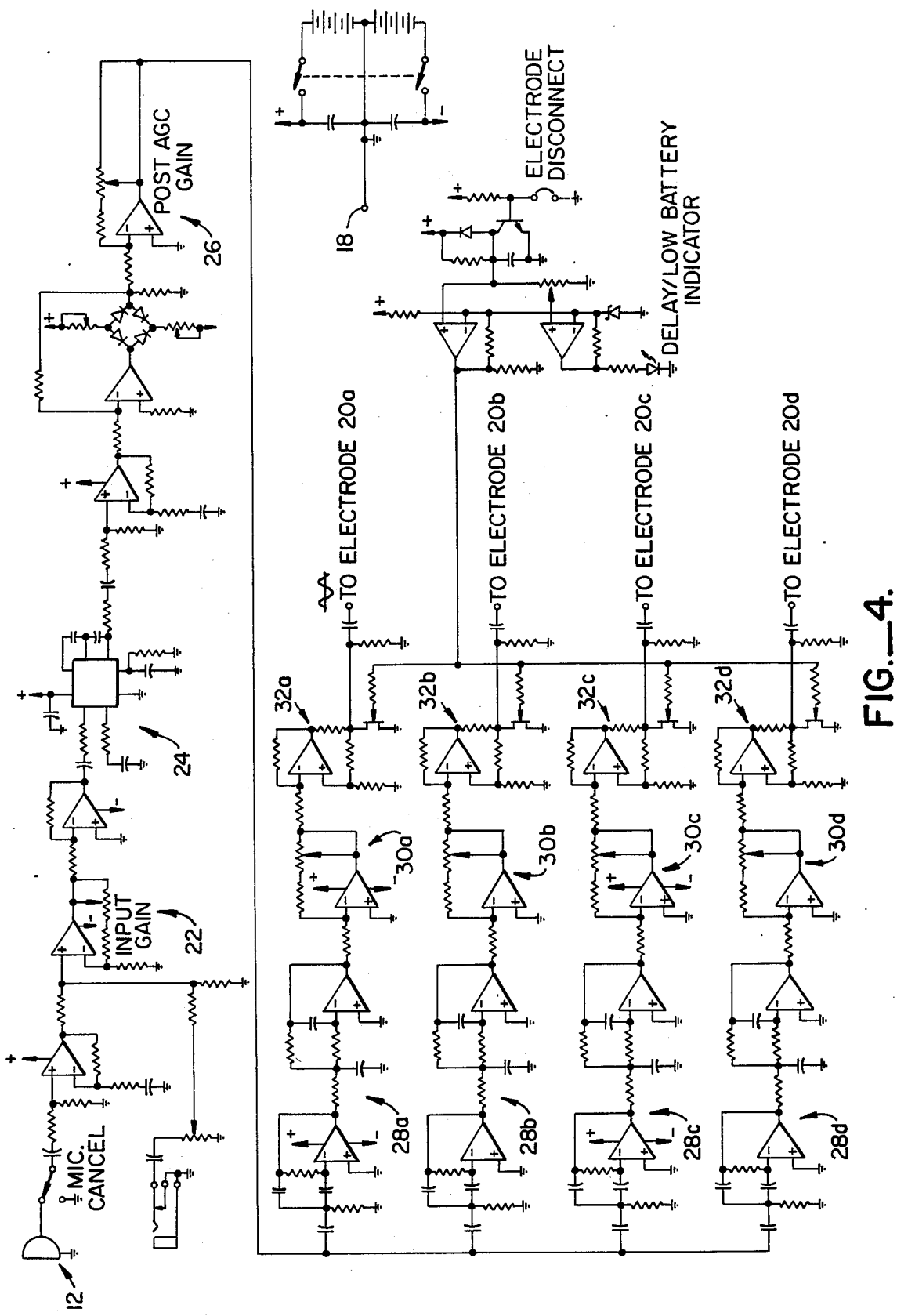
FIG._4.

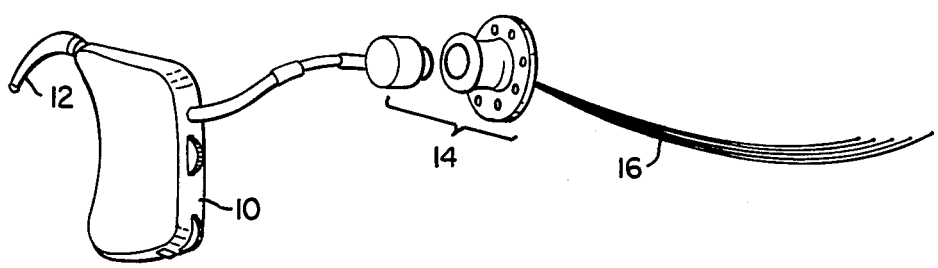
FIG._5.
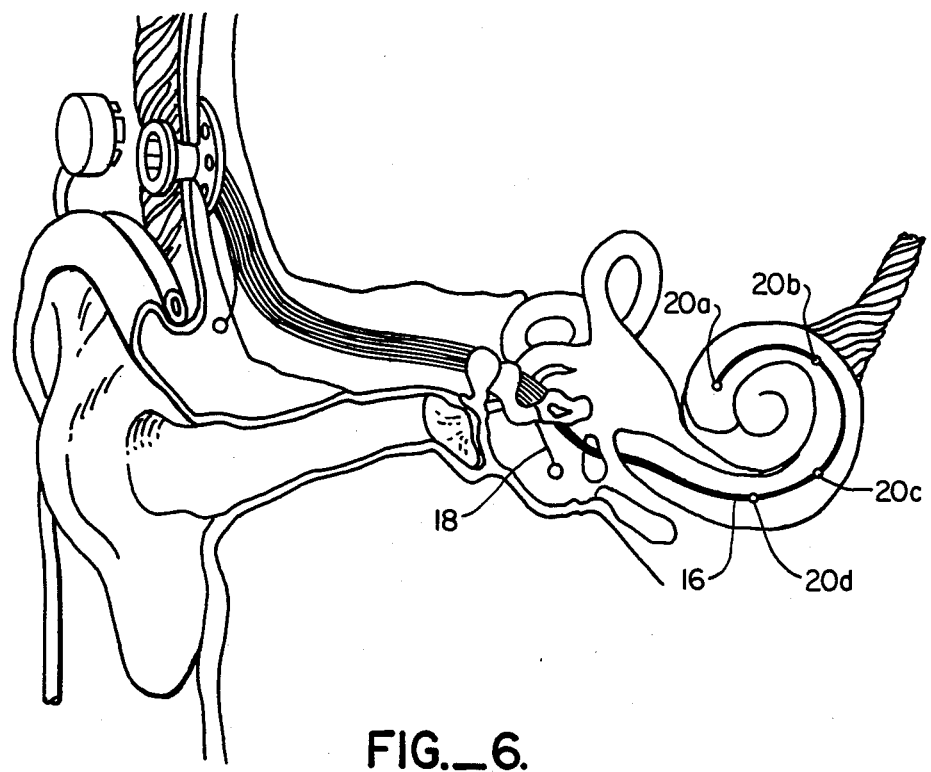
FIG._6.

ARTIFICIAL HEARING DEVICE AND METHOD

BACKGROUND ART

This invention relates to an electronic hearing device for stimulating the auditory nerve of a human patient by way of implanted electrodes. Such devices are necessary for people who have malfunctioning or non-functioning inner ear mechanisms.

There are some prior art devices which receive sound signals, convert said sound signals to electrical signals, divide those signals into channels based on frequency separation, and then apply the outputs of those channels to separate electrodes along the basilar membrane within the cochlea of a human patient. Many, if not most of those devices, involve the conversion of sound signals into digital electronic signals which are applied to the electrodes. Some systems, however, such as U.S. Pat. Nos. 3,751,605 and 4,400,590 apply analog signals representative of sounds to the auditory nerve.

In the normal ear, auditory nerve fibers are distributed along the cochlear basilar membrane. Because of the mechanical tuning of this membrane and its associates structures, nerve fibers that innervate near the basal end are sensitive to high frequencies while the more apical fibers are sensitive to lower frequencies. A multichannel device for auditory nerve stimulation that uses a plurality of filters to produce a plurality of component signals having different frequency ranges should distribute these component signals to electrodes in a relationship that is consistent with the frequency analysis preformed by the normal cochlea. Assume, for instance, that four channels of filter processing are used to produce four component signals named S1, S2, S3 and S4 with S1 having the lowest range of frequencies, S2 the next lowest, S3 the next lowest and S4 the highest range. These signals should be distributed to corresponding electrodes E1, E2, E3, E4, where E1 is placed in the cochlea more apical than E2, E2 more apical than E3 and E3 more apical than E4. Ideally, the position of E1 in the cochlea would correspond to the position of auditory neurons that are most sensitive to the center frequency of the channel that produces S1. Likewise for the other channels and their corresponding electrode positions.

It has been discovered that the amount of amplification necessary for each of the frequency channels is not necessarily uniform. In the Michelson Pat. No. 4,400,590, the gains of the respective channels are empirically adjusted to meet the particular needs of the user. This is an extremely difficult task since the user has no basis of comparison by which to tell the proper adjustment. Also, the adjustment is difficult to make with regard to discriminating speech sounds, which vary widely in frequency content.

SUMMARY OF THE INVENTION

The above and other problems of prior art hearing devices are overcome by the present invention of a multi-channel hearing device of the type which amplifies electrical signals which are representative of sounds, as, for example, for the transducer, and supplies such signals to the auditory nerve of a user through a plurality of electrodes implanted in the user's cochlea. The improvement of the present device comprises bandpass filter means for separating the electrical signals into a plurality of component signals having different frequency ranges within the audio spectrum, each of the ranges having a predetermined center frequency, and voltage source to current source converter means connected to the bandpass filter means for separately converting said signals into electrical currents representative of the frequency component signals of the original sounds. These currents are supplied to separate, implanted electrodes. An emphasis circuit, connected in series with the bandpass filter means causes the amplitudes of the frequency component signals, beyond what is necessary to produce a predetermined threshold response in the user, to increase at a predetermined rate of between 3 dB/octave and 9 dB/octave and preferably at about 6 to 7 dB/octave from the lowest center frequency to the highest center frequency of the component signals.

The respective center frequencies of the bandpass filter means of the preferred embodiment are approximately 500 Hz, 1000 Hz, 2000 Hz, and 4000 Hz.

In the preferred embodiment, connected in series with each voltage source to current source converter is an adjustable gain amplifier. Establishing a threshold amplitude for each electrode is accomplished by applying a particular standard stimulus, for example, a 200 Hz biphasic signal to the input of each adjustable gain amplifier and adjusting the gain until some standard threshold, patient response is obtained, for example, the softest audible tone with a 50% accuracy of detection.

Accordingly, it is an important object of the present invention to provide a hearing device for stimulating the auditory nerve which provides for high speech discrimination.

It is yet another object of the present invention to provide a hearing device for stimulating the auditory nerve which is relatively insensitive to the degree of coupling between the electrode and the auditory nerve.

The foregoing and other objectives, features and advantages of the invention will be more readily understood upon consideration of the following detailed description of certain preferred embodiments of the invention, taken in conjunction with the accompanying drawings.

BRIEF DESCRIPTION OF THE DRAWINGS

FIG. 1 is a block diagram of the hearing device according to the present invention.

FIG. 2 is a diagram illustrating the magnitude of frequency response of the respective bandpass filters shown in FIG. 1.

FIG. 3 is a graph illustrating the relative channel gain with respect to the logarithms of the channel center frequencies.

FIG. 4 is a detailed schematic diagram of the hearing device according to the invention.

FIG. 5 is a perspective view of the hearing device of the invention together with a cochlear implantable electrode assembly.

FIG. 6 is a diagrammatic view showing the installation of the implanted electrodes in the cochlea of a patient.

DETAILED DESCRIPTION OF THE PREFERRED EMBODIMENT

Referring now more particularly to FIGS. 5 and 6, the general physical assembly and installation of the hearing aid device according to the present invention is illustrated. A sound processor 10 is connected between a microphone assembly 12 and a percutaneous connector 14. In alternative embodiments, the percutaneous connector 14 could be replaced with a transcutaneous transmitter and a receiver. An electrode assembly 16 is connected to the female portion of the percutaneous connector. As shown in FIG. 6, the electrode assembly 16 is inserted into the cochlea so that the electrodes 20a, 20b, 20c, and 20d are disbursed along the length of the basal membrane. The electrodes may be uniformly spaced or spaced according to the patient's individual auditory response characteristics to the bandpass center frequencies. One or more electrodes 18 are used as grounds. A particularly satisfactory ground is the temporalis muscle. The remaining electrodes 20a-20d, inclusive, are inserted through the round window, into the scala tympani of the cochlea. The first electrode, namely electrode 20a, is inserted as far as possible, typically 24 mm.

Each electrode is formed by flaming a 0.5 mm ball on the end of a platinum wire (99% platinum). The platinum wire is 0.005 inches in diameter and is covered with an insulation of 2.5 mil thick layer of polytetrofluoroethylene (known under the trademark as TEFLON), extruded onto the platinum wire. While a particular electrode assembly has been described, other electrode designs could also be suitable for use with the present invention.

Referring now more particularly to FIGS. 1 and 4, the microphone 12 converts the sound signals into electrical signals which are supplied to the input of a first adjustable gain amplifier 22 which controls the level of background sound that is audible. With this gain turned down, only the loudest sounds will be within the capture range of the automatic gain control 24 which is connected to the output of the amplifier 22. When the gain of the amplifier 22 is at maximum, most signals produced by sounds audible to a normal hearing listener will be within the capture range of the AGC 24 and therefore audible to the patient. This control should not be confused with a loudness control which will be discussed hereinafter. The control 22 gives the patient the ability to mute background sounds that are softer than the signal of interest.

The automatic gain control 24 automatically adjusts its gain based on the input signal level. If the input signal varies slowly in amplitude within the "capture range" at the AGC, it will appear at the output as a signal of constant level. The characteristics of the circuit are used to perform two functions:

1. To reduce the dynamic range of the electrical waveforms used as stimuli to the ear. The dynamic range of the normal ear is more than 100,000. The dynamic range for electrical stimulation is typically less than 10 times threshold.

2. In conjunction with the preceding variable-gain stage, the AGC 24 gives the patient the ability to eliminate some background sounds.

Because the AGC cannot adjust its gain instantaneously, there is a chance that very sharp, loud sounds may slip through without proper attenuation. A clamp circuit built into the AGC sets a limit on the maximum signal level passed to the output of the AGC circuit 24.

The output at the AGC 24 is supplied to the input of a second variable gain amplifier 26 which is essentially the loudness control. When the patient increases this gain, the sounds he perceives become louder.

The output of the variable gain amplifier 26 is supplied to the inputs of four separate channels which separate the signals by frequency and individually amplify them. Each of the channels, for example the channel connected to electrode 20a is comprised of a bandpass filter 28a connected in series with a variable gain amplifier 30a. The output of the amplifier 30a is supplied to a voltage source to current source converter 32a which drives the electrode 20a. Similarly, the second channel is comprised of a bandpass filter 28b, a variable gain amplifier 30b, and a voltage source to current source converter 32b which are all connected in series to an electrode 20b. The third channel is comprised of a bandpass filter 28c, a variable gain amplifier 30c, and a voltage source to current source converter 32c which are all connected in series to an electrode 20c. The fourth channel is comprised of a bandpass filter 28d, a variable gain amplifier 30d, and a voltage to current converter 32d which are all connected in series to an electrode 20d.

The filters are four-pole bandpass filters with cut-off frequencies as illustrated in FIG. 2. The center frequencies of the bandpass filters 28a, 28b, 28c and 28d are, respectively, approximately 500 Hz, 1K Hz, 2K Hz, and 4K Hz. While the above noted center frequencies are used in the preferred embodiment, they could be modified somewhat in other embodiments.

A distinguishing feature of the present invention from the prior art is the relative gains of each of the amplifiers 30a, 30b, 30c and 30d with respect to each other. While in prior art systems, such as that proposed by Michelson, these gains were individually adjusted empirically for each patient, the gains of the present system are adjusted with respect to each other to provide the most efficient discrimination for speech information. The gains are adjusted so that, when measured at the center frequency of the particular channel's bandpass filter and after being normalized with respect to the electrode's threshold to a 200 Hz stimulus signal, the gains will increase at approximately 6 to 7 dB/octave. This means that when each channel's dB gain is plotted versus the logarithm of the channel's center frequency, the result will be a sloped line 34 as illustrated in FIG. 3.

The purpose of converting the electrical signal output from the adjustable gain amplifiers 30a-30d to an electric current is so that the amount of electrical charge delivered to each electrode 20a-20d, respectively, depends only on the stimulation waveform and is not a function of electrode to tissue contact resistance.

The normalization procedure is necessary because the contact between the various electrodes and the tissue is not constant and can change depending on the position of the electrode and can also change with deterioration in the surrounding tissue. In order for the relative gain settings described above to provide the most efficient discrimination, each amplifier 30a-30d must first have its gain adjusted to meet a certain minimum threshold level. This threshold level can be determined, for example, by applying a stimulus signal having a predetermined frequency to a given electrode. The amplitude of the stimulus signal is then increased until a predetermined response from the patient is produced. For example, the amplitude is adjusted to produce the lowest audible sound as perceived by the patient. This can be done by the ascending or descending methods, for example. See Eddington, D. K., et al.: *Auditory Protheses Research with Multiple Channel Intracochlear Stimulation in Man, The Annals of Otology, Rhinology & Laryngology,* Supplement 53, Volume 87, Nov.–Dec., 1978, No. 6, part 2, p. 17. After adjustment for the threshold level, the gains are then further adjusted according to the 6-7 dB/octave ratio.

Consider for example the case where all the electrodes 20a-20d have the same threshold characteristics for a 200 Hz stimulus. Such a stimulus signal may be a sinusoidal or, for example, a biphasic, pulsatile, current waveform of 50 micro-amperes (peak to peak) and 0.25 ms pulse duration.

Assume that each electrode requires no individual threshold gain adjustment, i.e. that all have the same threshold. For this situation, the proper gain adjustments for each channel would result in the following measurements at the outputs of the four channels:

TABLE I

| BAND-PASS CHAN-NEL | INPUT SIGNAL | | OUTPUT SIGNAL AMPLITUDE AS ADJUSTED |
|---|---|---|---|
| | AMPLITUDE | FREQUENCY | |
| 28a | 1 volt | 500 Hz | 50 μA |
| 28b | 1 volt | 1000 Hz | 100 μA |
| 28c | 1 volt | 2000 Hz | 200 μA |
| 28d | 1 volt | 4000 Hz | 400 μA |

This reflects the relative gains increasing by 6 dB/octave.

Now suppose that the threshold of electrode 20c to a 200 Hz stimulus signal increases from 50 μA to 200 μA (by a factor of 4). If the relative channel gains are left as depicted in TABLE I, the "effective" stimulus at electrode 20c would not be the same. The gain of channel must be adjusted upwards to reflect the high threshold of electrode 20c. It must, in fact, be increased by a factor of 4. This setting results in a relationship between the channel gains of 6 dB/octave, normalized for the relative thresholds of the electrodes:

TABLE II

| BAND-PASS CHAN-NEL | INPUT SIGNAL | | OUTPUT SIGNAL AMPLITUDE AS ADJUSTED |
|---|---|---|---|
| | AMPLITUDE | FREQUENCY | |
| 28a | 1 volt | 500 Hz | 50 μA |
| 28b | 1 volt | 1000 Hz | 100 μA |
| 28c | 1 volt | 2000 Hz | 800 μA |
| 28d | 1 volt | 4000 Hz | 400 μA |

This process for a 6 to 7 dB/octave, normalized relationship can be stated mathematically in the following manner:

Let
$G_i$ = gain of the channel associated with electrode i.
$T_i$ = the threshold measured at electrode i with a standard stimulus (say 200 Hz, biphasic pulsatile waveform).
$F_i$ = the center frequency of the bandpass filter associated with electrode i.
$G_a$ = gain of channel a.
$F_a$ = bandpass center frequency of channel a.
$T_a$ = threshold measured at electrode 20a with the standard stimulus.

$$G_i = \left(\frac{T_i}{T_a}\right) \times \left(\frac{F_i}{F_a}\right) \times G_a$$

While in the above-described embodiment each channel was provided with a bandpass filter whose output was supplied to the input of a variable gain amplifier, it should be apparent that, in other embodiments, the series arrangement of the bandpass filters and the individually adjustable gain controlled amplifiers could be reversed so that the bandpass filters were interposed between the adjustable gain amplifiers and the voltage source to current source converters.

In another embodiment, the adjustment of the relative mean amplitudes of the frequency components of the electrical signals representing the sound signals does not take place in the separate channels defined by the series circuits of elements 28a-32a, 28b-32b, 28c-32c, 28d-32d, respectively. Instead, the amplifier 26 is designed to have a pre-emphasis of 6 to 7 dB/octave, i.e. the response of the amplifier is frequency dependent so that more gain is given to the higher frequencies at the rate of 6 to 7 dB/octave from the lowest center frequency of 500 Hz to the highest center frequency of 4000 Hz. Thereafter, the bandpass filters 28a-28d, inclusive, separate the frequency components and apply them to the separate electrodes as described above. In this embodiment, the only adjustment made to the gains of amplifiers 30a-30d, inclusive, is the threshold adjustment described above. In still other embodiments, this desired pre-emphasis can be obtained by passive circuits comprised of known filtering networks.

While it was found that the best results were obtained by adjusting the relative amplitudes to follow a 6 to 7 dB/octave ratio, in other, less effective embodiments, this range could fall within 3 dB/octave to 9 dB/octave. As the relative ratio falls towards these extremes, however, the ability to recognize speech signals deteriorates significantly.

In the above embodiments, only four electrodes and four bandpass filters are shown and described, with the center frequencies of the bandpass filters 28a-28d being spaced apart by whole octaves. It should be understood that in other embodiments more electrodes and more channels could be used. In such case, the center frequencies of the bandpass filters would be uniformly distributed over the logarithmic frequency range of at least 500 Hz to 4000 Hz and the emphasis given to the amplitudes would be at the above described ratio of 6 to 7 dB/octave, taking into account the less than whole octave separation of the channels. Thus, the same relationship between channel gain and channel center frequency as depicted in FIG. 3 would be maintained.

While the invention has been described in terms of a device for detecting and hearing sounds, it should be apparent that the microphone 12 could be replaced by, for example, a connection to a telephone, a radioreceiver, or any other source of electrical signals representative of sounds.

The terms and expressions which have been employed here are used as terms of description and not of limitations, and there is no intention, in the use of such terms and expressions, of excluding equivalents of the features shown and described, or portions thereof, it being recognized that various modifications are possible within the scope of the invention claimed.

I claim:
1. A multichannel hearing device of the type which amplifies electrical signals which are representative of sounds and supplies said signals to the auditory nerve of a user through a plurality of electrodes implanted in the cochlea, wherein the improvement comprises
bandpass filter means for separating said electrical signals into a plurality of frequency component signals having different frequency ranges within the audio spectrum, each of the ranges having a predetermined center frequency, voltage source to current source converter means connected to the bandpass filter means for separately converting said signals to electric currents representative of the frequency component signals of the original sounds, and for supplying the electric currents to separate ones of the implanted electrodes, emphasis means connected in series with the bandpass filter means and the voltage source to current source converter means for causing the amplitudes of said frequency component signals, beyond what is necessary to produce a predetermined threshold response in the user, to increase at a predetermined number of dB per octave from the lowest center frequency to the highest center frequency of the component signals.

2. A hearing device as recited in claim 1 wherein the predetermined number of dB is between 3 and 9.

3. A hearing device as recited in claim 1 wherein the predetermined number of dB is between 6 and 7 dB.

4. A multichannel hearing device as recited in claim 1 wherein the respective center frequencies of the bandpass filter means comprise 500 Hz, 1000 Hz, 2000 Hz, and 4000 Hz.

5. A multichannel hearing device as recited in claim 1 wherein the emphasis means includes a plurality of adjustable gain amplifiers, each being connected to a separate one of the voltage source to current source converter means and wherein the gain (Gi) of the adjustable gain amplifier connected to electrode i is determined by the relationship:

$$Gi = Ga\left(\frac{Ti}{Ta}\right) \times \left(\frac{Fi}{Fa}\right)$$

where
Ti = the threshold current measured at the electrode i with a predetermined stimulus signal,
Fi = the center frequency of the bandpass filter means connected to said adjustable gain means,
Ga = the gain of the adjustable gain means associated with the lowest center frequency (Fa), and
Ta = the threshold current measured at the electrode associated with the lowest center frequency when supplied with the predetermined stimulus signal.

6. A hearing device as recited in claims 1, 2, 3 or 5 further comprising an automatic gain control and limiter circuit for limiting the dynamic range and maximum signal level of the electrical signals representative of sounds to no greater than that amplitude required to elicit sound percepts of maximum comfortable loudness in the user.

7. A hearing device as recited in claims 1, 2, 3 or 4 further comprising means connected to each voltage source to current source converter means for separately providing a threshold normalizing level of amplification of the frequency component signals, said threshold normalizing level of amplification being that which makes a stimulus signal having a predetermined frequency and magnitude just audible to the user.

8. A method of artificially stimulating the auditory nerve of a patient with electric currents applied through a plurality of electrodes comprising the steps of converting sound signals into corresponding electrical signals, emphasizing the amplitudes of said signals to cause their amplitudes, beyond what is necessary to produce a predetermined threshold response in the patient, to increase at a predetermined number of dB per octave with frequency, separating said electrical signals into a plurality of ranges of component frequencies within the audio spectrum, each of said ranges having a different predetermined center frequency, producing electric currents corresponding to the separated electrical signals and supplying them to the separate electrodes.

9. The method as recited in claim 8 further comprising the step, prior to emphasizing the electrical signals, of first determining a threshold amplification for each electrode which is necessary to produce a predetermined response in the patient to a predetermined stimulus applied to that electrode, and, thereafter, as the emphasizing step, adjusting the relative ratios of the threshold amplifications to be a predetermined number of dB/octave from the lowest center frequency to the highest center frequency.

10. The method as recited in claim 8 wherein the step of separating the electrical signals comprises the steps of separating them into ranges having center frequencies of 500 Hz, 1000 Hz, 2000 Hz, and 4000 Hz.

11. The method as recited in claims 8 or 9 wherein the emphasizing step comprises causing the mean amplitudes of the separated electrical signals to increase at the rate of between 6 to 7 dB/octave from the lowest center frequency to the highest center frequency.

12. A method for inducing hearing by electrical stimulation of the auditory nerve of a patient by use of two or more electrodes implanted in the cochlea of the patient, comprising the steps:

converting sound signals to be heard to corresponding electrical signals;

separating said electrical signals into separate frequency channels;

adjusting the gain of each channel independently of the other channels; and providing the electrical signals in each channel to selected ones of said two or more electrodes;

wherein the improvement comprises adjusting the gain of each channel in two steps, said two steps comprising:

adjusting the gain of each channel to a threshold gain such that an electrical signal of predetermined frequency and amplitude applied to each channel evokes a minimum threshold response in the patient; and superimposing on the threshold gain an additional gain, said additional gain varying from channel to channel in a manner so as to increase in a predetermined relationship with the frequency of the electrical signals within the channel.

13. A method for inducing hearing as set in claim 12 wherein said predetermined relationship is a rate of increase within the range 3 to 9 decibels per octave.

14. A method for inducing hearing as set out in claim 12 further including the step of converting said electrical signals in each channel to current signals prior to providing said electrical signals to said electrodes.

15. A method for inducing hearing as set out in claim 12 wherein said predetermined relationship is a rate of increase between 6 and 7 decibels per octave.

16. A method for inducing hearing as set out in claim 12 wherein said electrical signals within each channel are within a frequency range centered around a center frequency and wherein said predetermined relationship is the following:

$$Gi = Ga \times (Fi/Fa)$$

where
- $Gi$ = the gain of channel i,
- $Fi$ = the center frequency of channel i,
- $Ga$ = the gain of the channel having lowest center frequency, and
- $Fa$ = the center frequency of channel a.

17. An artificial hearing device for inducing hearing by electrical stimulation of the auditory nerve of a patient, comprising:

transducer means for converting sound signals to corresponding electrical signals;

means for separating said electrical signals into separate channels based on frequency;

a plurality of electrodes implantable within the cochlea of the patient;

first adjustable gain means connected in series with said means for separating and said electrodes for providing a threshold gain such that an electrical signal of predetermined frequency and amplitude applied to each channel evokes a minimum threshold response in the patient;

second adjustable gain means for providing an additional gain in each channel beyond the threshold gain such that the additional gain varies from channel to channel so as to increase in a predetermined relationship with the frequency of the electrical signals within a channel.

18. An artificial hearing device as set out in claim 17 wherein said second adjustable gain means is connected in series between said transducer means and said means for separating and comprises an amplifier having a frequency dependent gain increasing at the rate of from 6 to 7 decibels/octave throughout the audible frequency range.

19. An artificial hearing device as set out in claim 17 wherein said second adjustable gain means comprises a plurality of amplifiers having fixed gains connected in series with said means for separating and said electrodes, each amplifier being associated with a channel and thereby with a frequency or range of frequencies and wherein the fixed gain of each amplifier are predetermined to vary relative to each other at a rate of between 6 and 7 decibels per octave.

* * * * *